(12) United States Patent
Bertrand et al.

(10) Patent No.: US 9,241,985 B2
(45) Date of Patent: Jan. 26, 2016

(54) LIVE VACCINE FOR AVIAN DISEASES

(75) Inventors: Francois Bertrand, Paris (FR); Sebastien Deville, Paris (FR); Laurent Dupuis, Reims (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 417 days.

(21) Appl. No.: 13/581,413

(22) PCT Filed: Mar. 15, 2011

(86) PCT No.: PCT/FR2011/050515
§ 371 (c)(1),
(2), (4) Date: Aug. 27, 2012

(87) PCT Pub. No.: WO2011/117507
PCT Pub. Date: Sep. 29, 2011

(65) Prior Publication Data
US 2012/0321663 A1 Dec. 20, 2012

(30) Foreign Application Priority Data

Mar. 24, 2010 (FR) ..................... 10 52113

(51) Int. Cl.
| | |
|---|---|
| *A61K 39/215* | (2006.01) |
| *A61K 39/295* | (2006.01) |
| *A61K 39/17* | (2006.01) |
| *A61K 39/12* | (2006.01) |
| *A61K 39/00* | (2006.01) |

(52) U.S. Cl.
CPC ......... *A61K 39/12* (2013.01); *A61K 2039/5254* (2013.01); *A61K 2039/552* (2013.01); *A61K 2039/55566* (2013.01); *A61K 2039/70* (2013.01); *C12N 2760/18134* (2013.01); *C12N 2770/20034* (2013.01)

(58) Field of Classification Search
None
See application file for complete search history.

(56) References Cited

U.S. PATENT DOCUMENTS

| | | | |
|---|---|---|---|
| 4,650,677 A | | 3/1987 | Roerink |
| 4,795,635 A | * | 1/1989 | Peleg et al. ................ 424/214.1 |
| 2006/0233831 A1 | * | 10/2006 | Parisot et al. .............. 424/204.1 |
| 2010/0233196 A1 | * | 9/2010 | Dupuis et al. .............. 424/184.1 |

FOREIGN PATENT DOCUMENTS

| | | | |
|---|---|---|---|
| WO | 2005/009462 A2 | | 2/2005 |
| WO | 2009/053601 A2 | | 4/2009 |
| WO | WO 2009/053601 | * | 4/2009 |

OTHER PUBLICATIONS

International Search Report dated Jun. 17, 2011, from corresponding PCT application.

* cited by examiner

*Primary Examiner* — Shanon A Foley
*Assistant Examiner* — Myron Hill
(74) *Attorney, Agent, or Firm* — Young & Thompson

(57) ABSTRACT

A method for preparing a vaccine composition to be implemented in a locally administered treatment for avian viral disease, includes at least the step of: a) extemporaneously mixing a vaccine, including at least one live virus selected from a virus belonging to one or more strains of the avian disease, with an adjuvant diluent (DA), characterized in that the adjuvant diluent is a continuous aqueous phase oil-in-water emulsion or oil-in-water microemulsion.

8 Claims, No Drawings

LIVE VACCINE FOR AVIAN DISEASES

FIELD OF THE INVENTION

The present invention relates to a method for preparing a vaccine composition used in a locally administered treatment for avian viral diseases and in particular avian infectious bronchitis.

BACKGROUND OF THE INVENTION

Avian infectious bronchitis is an acute and contagious disease which affects poultry mainly through respiratory symptoms. The avian infectious bronchitis virus (or IBV) is a member of the Coronavirus genus, family Coronaviridae, order Nidovirales. This single-stranded RNA virus has a strong capacity for evolution, and the viral particles can survive for a period of one month in the outside environment. IBV affects poultry of all ages and does not target only the respiratory tracts. Indeed, IBV replicates first of all in the trachea and can subsequently spread throughout the body of the affected fowl, affecting various internal organs.

Morbidity is high and mortality can vary according to farms, to farming conditions and also to sites of bacterial superinfections.

The clinical signs are of the following types:
respiratory (coughing, tracheal rales, swollen sinuses, conjunctivitis, etc.);
reproductive (decrease in egglaying, production of eggs with thin, deformed or colored shells);
renal, intense thirst, etc.

IBV is transmitted especially by the respiratory pathway, or via aerosols. The virulent materials are made up of nasal discharge and droppings. Transmission is horizontal, directly (from sick birds to sensitive birds), or indirectly (via water, material, etc.).

IBV is sensitive to most disinfectants, but the best means of containment consists of vaccination allied to taking biosafety steps (decontamination steps, disinfection steps, etc.).

Vaccination consists in inoculating the species to be protected with an amount of killed pathogen (inactivated vaccine) or pathogen of which the virulence has been reduced (live attenuated vaccine) in order to trigger a biological response in the host, protecting it during the subsequent occurrence of the disease.

Live vaccines are generally sufficiently effective so as not to require the use of adjuvants.

A vaccine adjuvant is an excipient which amplifies the biological response against the antigen with which it is combined. Mention will be made, for example, of aluminum hydroxide, and the oily adjuvants sold under the name Montanide™ by the company SEPPIC. These adjuvants are of various natures. They can just as well consist of liposomes, of emulsions comprising at least one oily phase and at least one aqueous phase, of the "Freund's" adjuvant type, or more commonly of water-insoluble inorganic salts. Among the inorganic salts used as vaccine composition adjuvants, mention may, for example, be made of aluminum hydroxide, cerium nitrate, zinc sulfate, colloidal iron hydroxide or calcium chloride. Aluminum hydroxide is the adjuvant most commonly used. These inorganic salts used as vaccine composition adjuvants are described in particular in the article by Rajesh K. Gupta et al., "Adjuvants, balance between toxicity and adjuvanticity", Vaccine, vol. 11, Issue 3, 1993, pages 293-306.

Vaccines can be administered by injection (subcutaneous or intramuscular injection) or locally (mass vaccination by nebulization, addition to the drinking water for contact with the beak and nostrils and the oculonasal complex, for example). Vaccination by injection, even if it proves to be effective, has the drawback of not being suitable for the economic context of poultry farms (high labor cost), and it also causes stress in the poultry treated, which, in the case of egg-layers, can lead to disruptions in egglaying following the physical trauma caused by the injection.

The use of effective adjuvants in vaccine compositions, and in vaccine compositions intended for preventing the occurrence of infectious bronchitis, makes it possible:
to increase the strength of the protective response, making it possible to provide a better level of protection;
to prolong the duration of the protection conferred by a vaccine dose, providing longer-lasting protection of the animals in farms throughout their growth;
to provide sufficient protection with a single treatment when two treatments were necessary in the absence of these immune response amplifiers. The saving is then in the number of doses to be injected (halved), the handling of the animals (labor) and the stress caused during the handling of the animals (also halved);
to have the possibility of obtaining, with a lower antigenic dose, an efficacy equivalent to that conferred by a complete dose used without adjuvant. Thus, the vaccine production plant will, with the same productive capacity, be capable of producing a higher number of vaccine doses. Likewise, an existing packaging may be proposed for vaccinating a larger number of animals.

No adjuvant is described or used at the current time during the implementing of vaccination techniques by local administration using live vaccines.

There is a need to develop diluents which also have the adjuvant function for improving the immune response as described above. These compositions are referred to as adjuvant diluents (ADs).

The main difficulty encountered in the development of an AD is the ability of said adjuvant diluent (AD) to keep the live vaccine alive so that it retains its immunogenic properties.

An important element of the development of adjuvants for live vaccines lies in the specificity of the adjuvant formulations for not killing the live microorganisms constituting the vaccine antigens when they are brought into contact before injection. ADs exist on the market (such as, for example, tocopheryl acetate from the company Intervet included in Diluvac Forte®) and are recommended for certain live vaccines.

Furthermore, a live vaccine is known in French patent application FR 2 385 401.

However, this live vaccine is not prepared with adjuvant substances. It has up until now been taken as read that the greater immune response could be produced with a live vaccine, for example, by increasing the content of virus, or by using a more immunogenic strain.

SUMMARY OF THE INVENTION

According to the present invention, a method for preparing a live virus vaccine has been found, which is characterized in that the live vaccine is prepared by means of an adjuvant of the continuous aqueous phase emulsion type, for example a water-in-oil emulsion or microemulsion.

It has surprisingly been noted that the use of an oil-in-water (O/W) emulsion as a "diluent" for live vaccines has a positive effect on the serological and immune response in the vaccinated animals. In this oil-in-water emulsion, the external aqueous phase allows the vaccine (generally freeze-dried) to be easily dissolved.

Another aspect of the invention is that the use of the oil-in-water emulsion as adjuvant diluent for live vaccines causes a very high serological response in young animals which still have maternal immunity. This surprising effect may be caused by the protective action of the emulsion, on the live virus, against neutralization by the antibodies present in the animal.

One objective of the present invention is to overcome all or some of the drawbacks of the prior art noted above.

To this end, a subject of the present invention is a method for preparing a vaccine composition used in a locally administered treatment for an avian viral disease, comprising at least the step of:

a) extemporaneously mixing a vaccine, comprising at least one live virus selected from a virus belonging to one or more strains of said avian disease, with an adjuvant diluent (AD), characterized in that said adjuvant diluent is an oil-in-water continuous aqueous phase emulsion or an oil-in-water microemulsion.

DETAILED DESCRIPTION OF THE INVENTION

The term "avian viral disease" is intended to mean:
respiratory viral diseases, such as, for example, infectious laryngotracheitis, avian infectious bronchitis, pigeon herpesvirus infection, turkey rhinotracheitis;
digestive viral diseases, such as, for example, duck plague, duck viral hepatitis, avian hepadnaviruses;
viral skin diseases, such as, for example, avian pox;
viral diseases of the nervous system, such as, for example, avian encephalomyelitis, eastern equine encephalitis, West Nile fever, rabies, "louping-ill";
systemic viral diseases such as, for example, avian pseudo-plague (Newcastle disease), Marek's disease, Gumboro disease, fowl plague, avian leukosis, chicken infectious anemia, Derszy's disease, "soft-egg" disease.

The term "diluent" is intended to mean a substance to be added to another in order to reduce the titer, the richness or the percentage thereof.

An adjuvant diluent for locally administered vaccine (AD-LAV) will, in order to be relevant, have to:
keep the vaccine alive, after reconstitution, for a given period of time;
allow the preparation of a formula (vaccine composition) which is easily sprayable and wetting for the mucus membranes (of hydrophilic nature) so as to allow an effective and easy treatment;
significantly improve the immune effectiveness of the antigen compared with that of the antigen used without adjuvant, and without causing side effects.

Moreover, embodiments of the invention may comprise one or more of the following characteristics:
method as defined above, characterized in that said virus contained in said vaccine belongs to one or more strains of IBV (infectious bronchitis virus);
method as defined above, characterized in that said virus contained in said vaccine is a Newcastle disease virus;
method as defined above, characterized in that said virus contained in said vaccine belongs to one or more strains of IBV (infectious bronchitis virus), a Newcastle disease virus, or a mixture of these viruses.

Newcastle disease, also known as "avian pseudo-plague", "avian pneumoencephalitis" or "Ranikhet disease", is a bird zoonosis caused by a virus.

The morbidity and mortality vary greatly depending on the virulence of the strain, the immunity and the condition of the animal and other environmental factors.

The Newcastle disease virus is a virus of the family Paramyxoviridae, of the Rubulavirus genus.

It is an RNA virus with a single strand (unlike influenza, which has eight strands), termed single-stranded. RNA viruses mutate readily and often, which can make pharmaceutical and vaccine strategies more complex and difficult.

The envelope, which has a diameter of from 150 to 300 nm, has two types of glycoprotein spicules. It is characterized by:
An HN glycoprotein, which has the hemagglutinating and neuramidase activities, allowing attachment of the virion to membrane receptors at the surface of the cell and its release;
An F glycoprotein which allows fusion between the viral envelope and the cell membrane.

The virus is easily cultured in embryonated hen eggs or in vitro (on chicken embryo fibroblasts or on chicken renal cells).

The virus is very resistant at ambient temperature, it remains infectious:
for a long time (several months) in fecal matter,
for 2 to 3 months on the ground, in a henhouse,
for 7 to 8 months on a soiled shell,
for 2 years and more in an uncooked and frozen carcass.

As for influenza, the strains are classified according to their virulence, by distinguishing:
velogenic strains (highly virulent, inducing mortality approaching or reaching 100%, with an attack which is systemic, or at least visceral or involving the nervous system, possibly associated with respiratory problems),
mesogenic strains (moderately virulent) producing a respiratory ailment with nervous system problems, for a mortality reaching 50% in young birds,
lentogenic strains (weakly virulent, non-mortal, producing some respiratory problems, and sometimes inducing no symptom). These are, for example, the Hitchner B1 and La Sota strains.

The sources of the virus are linked to the organs targeted by the virus, which vary depending on viral strain, and the condition and immune history of the affected bird, which will express the virus in:
the bronchial secretions and fecal matter,
all parts of the carcass.

The viruses are excreted from the beginning of incubation and over a variable period during convalescence, a few days to two weeks, in rare cases more.

To combat the virus, precautionary and preventive measures exist which can be implemented by the farmer, which can, for example, consist of placing the infected animals in quarantine, of euthanasia of the infected animals, of hygiene measures, and of disinfection and regular cleaning of the premises with conventional disinfectants.

Vaccination also constitutes a means of prevention.

A subject of the invention is also:
A method as defined above, characterized in that the adjuvant diluent (AD) comprises an oily adjuvant, an aqueous phase, at least one divalent inorganic salt and at least one complexing agent;
A method as defined above, characterized in that the virus contained in said live vaccine is freeze-dried before step a).

Live vaccines are generally stored freeze-dried and must be resuspended extemporaneously with an aqueous phase. The vaccine thus reconstituted must be used within hours following the addition of a diluent.

A method as defined above, characterized in that said adjuvant diluent is an oil-in-water emulsion comprising, for 100% of its weight:
  from 50% to 97% of water, more particularly from 70% to 97% of water, and even more particularly from 80% to 97% of water;
  from 1% to 45% of oily adjuvant, more particularly from 1% to 30% of oily adjuvant, and even more particularly from 2% to 10% of oily adjuvant;
  from 0.1% to 10% of at least one divalent inorganic salt, more particularly from 0.1% to 8%, and even more particularly from 0.2% to 3%;
  from 0.1% to 10% of at least one complexing agent, more particularly from 0.1% to 8%, and even more particularly from 0.2% to 3%.

A method as defined above, characterized in that said adjuvant diluent is an oil-in-water microemulsion comprising, for 100% of its weight:
  from 50% to 97% of water, more particularly from 70% to 97% of water, and even more particularly from 80% to 97% of water;
  from 1% to 45% of oily adjuvant, more particularly from 1% to 30% of oily adjuvant, and even more particularly from 2% to 10% of oily adjuvant;
  from 0.1% to 10% of at least one divalent inorganic salt, more particularly from 0.1% to 8%, and even more particularly from 0.2% to 3%;
  from 0.1% to 10% of at least one complexing agent, more particularly from 0.1% to 8%, and even more particularly from 0.2% to 3%.

A method as defined above, characterized in that said oily adjuvant comprises, for 100% of its weight:
  from 40% to 95% of at least one mineral oil, more particularly from 50% to 95% of at least one mineral oil, and even more particularly from 50% to 90% of at least one mineral oil;
  from 5% to 60% of at least one surfactant, more particularly from 5% to 50% of at least one surfactant, and even more particularly from 10% to 50% of at least one surfactant.

A method as defined above, characterized in that said at least one divalent inorganic salt is selected from manganese gluconate, calcium gluconate, calcium aspartate, zinc gluconate, iron gluconate and A method as defined above, characterized in that said at least one complexing agent is selected from ethylenediaminetetraacetic acid (EDTA), sodium gluconate, potassium gluconate and sodium polyacrylate.

The mineral oils used for preparing the oily adjuvants are selected from the group consisting of hydrocarbon mineral oils obtained by distillation of oil and by implementing subsequent processing steps such as, for example, desulfurization, deasphalting, aromatic compound extraction and wax extraction steps, and other finishing processing steps (mention may, for example, be made of oils of the Marco) 52, MARCOL 82, Drakeol 5 and Drakeol 6, etc., type).

The surfactants present in the oily adjuvants are emulsifying surfactants having a hydrophilic nature characterized by an HLB value of between 8 and 19, more particularly between 8 and 15.

Such a surfactant may consist of an alkylpolyglycoside or a mixture of alkylpolyglycosides; saponins; lecithins; polyoxyethylated alkanols; polymers comprising polyoxyethylene and polyoxypropylene blocks; or esters obtained by condensation of a fatty acid, advantageously a fatty acid that is liquid at 20° C., with a sugar, sorbitol, mannitol or glycerol. Said sugar may consist of glucose or sucrose, or preferably mannitol. For preferred esters, mention may be made of esters of fatty acids, for instance oleic acid, stearic acid, palmitic acid or lauric acid, and of sorbitol or mannitol, obtained by esterification of the fatty acid with the sorbitol or the mannitol, or else by esterification with the products resulting from the anhydrization of the polyhydroxylated chain of sorbitol or of mannitol which cyclizes in position 1-4 or in position 2-6, or else by esterification with sorbitol or mannitol and with the products resulting from the anhydrization of the polyhydroxylated chain of sorbitol or of mannitol which cyclizes in position 1-4 or in position 2-6. As particularly preferred mannitol esters, mention may be made of mannitol oleates, mannitan oleates, ethoxylated mannitol oleates comprising 5 mol or 10 mol or 15 mol or 20 mol of ethylene oxide, and ethoxylated mannitan oleates comprising 5 mol or 10 mol or 15 mol or 20 mol of ethylene oxide. Polyethylene glycol, sorbitol or glycerol sugar ester derivatives may also be used. The other types of preferred surfactants consist of ethoxylated plant oils, for instance ethoxylated corn oils having between 3 mol and 40 mol of ethylene oxide, ethoxylated rapeseed oils having between 3 mol and 40 mol of ethylene oxide, or ethoxylated castor oils having between 3 mol and 60 mol of ethylene oxide.

EXAMPLES

The compatibility of the adjuvant formulae with the viability of freeze-dried vaccines is related to the composition of this adjuvant formula and to the level at which it is used. Biocompatible constituents combined in proportions providing good implementation and an adjuvant capacity were selected and this selection was then evaluated in quantitative study protocols. The viability of the adjuvanted vaccines (and therefore the compatibility of the formulations with the live vaccines) is necessarily good for vaccines having demonstrated an efficacy greater than a commercial reference.

Improvement of the efficacy is reflected, for the farmers, by better zootechnical performance levels, a lower cost for the treatments and time saved. Local treatments do not at the current time use performance-stimulating adjuvants.

A—Demonstration in the Case of Infectious Bronchitis
a) Products which are the Subjects of the Study
Various Adjuvant Diluents Prepared

TABLE I

|  | AD1 | AD2 | AD3 | AD4 | AD5 | AD6 | AD7 | AD8 | AD9 | AD10 | AD11 |
|---|---|---|---|---|---|---|---|---|---|---|---|
| Water Adjuvant: | 83% | 83% | 86% | 86% | 86% | 83% | 89% | 89% | 86% | 98% | 75% |
| Oil Marcol 52; ethoxylated | 5% | 5% | 5% | 5% | 5% | 5% | 5% | 5% | 5% | 0% | 15% |

TABLE I-continued

|  | AD1 | AD2 | AD3 | AD4 | AD5 | AD6 | AD7 | AD8 | AD9 | AD10 | AD11 |
|---|---|---|---|---|---|---|---|---|---|---|---|
| mannitan oleate HLB = 12 | 5% | 5% | 2% | 2% | 5% | 5% | 2% | 2% | 5% | 0% | 10% |
| Complexing agent | | | | | | | | | | | |
| EDTA | 0% | 0% | 0% | 0% | 2% | 0% | 2% | 0% | 2% | 0% | 0% |
| sodium polyacrylate | 5% | 0% | 5% | 0% | 0% | 0% | 0% | 0% | 0% | 2% | 0% |
| Mineral salt | | | | | | | | | | | |
| manganese gluconate | 2% | 2% | 2% | 2% | 2% | 2% | 2% | 2% | 0% | 0% | 0% |
| calcium gluconate | 0% | 0% | 0% | 0% | 0% | 0% | 0% | 0% | 2% | 0% | 0% |
| Physical form of the adjuvant diluent | m O/W | mO/W | O/W | O/W | m O/W | m O/W | O/W | O/W | m O/W | — | O/W | m O/W: O/W microemulsions
O/W: O/W emulsion

Various Vaccine Compositions Prepared

Antigen used: virus of the H-120 line of the B1 virus extracted from embryonated, specific pathogen free (SPF) chicken eggs with an effective infectivity titer of 7.0 Ig EID50/ml.

Each experimental vaccine (from VA1 to VA11, comprising respectively the adjuvant diluent AD1 to AD11) is prepared by adding:
- approximately 5% of the antigen (corresponding to the freeze-dried material of the antigen described above), and
- approximately 95% of the experimental adjuvant diluent (AD1 to AD11).

b) Measurements of Efficacy on Chickens

Experimental Protocol b1) The efficacy of each of the vaccine compositions (VA1 to VA11) was determined on groups of 10 chickens receiving a treatment of 100 μl of vaccine in each nostril (intranasal administration of 0.2 cm$^3$ of vaccine per animal).

Thus, the chickens of group i receive a treatment involving the VAi vaccine, with i=1 to 11. The chickens used in the context of this experiment come from a farm, are 22 days old, are seronegative for infectious bronchitis IB disease, and are of the High sex brown strain.

Furthermore:
- a group of 10 chickens (group 12), or positive control group, receives the administration, according to the same mode, of a commercial vaccine against infectious bronchitis. This commercial vaccine contains only water as diluent and no adjuvant nor any oil or surfactant.

As positive reference, a commercial vaccine produced by FGI "ARRIAH": IB strain H-120 batch 211 was used;
- a group of 10 chickens (group 13), or negative control group, receives no vaccination.

For each of the chickens of each group, blood samples were taken 7/14/21/28/35/42/49/56 days after the start of vaccination in order to quantify the antibody titers generated.

b2) Virulence Challenge 56 days after the date of the first vaccination, the protection generated by the vaccines is evaluated by carrying out a virulent challenge: for this, the animals are infected with a predetermined load of pathogen (using the pathogenic strain M-41 of the IB virus at a dose of 6.46 CD50 or 6.3 Ig EID 50).

The strength of the disease caused is evaluated by measuring:

1/ the cumulative strength of the points of each animal for 7 days following the infection, with a scoring scale (1 point: shortness of breath/2 points: shortness of breath and tracheal difficulties/3 points: respiratory distress, turgescent face, discharges, general symptoms). The longer a group is sick and the more sick the group is, the higher this score is;

2/ the sum of the days of the group during which the symptoms were observed: this score quantifies the ability of the animals to overcome the disease;

3/ the mean of the points with the standard deviation of the group making it possible to evaluate the homogeneity of the group;

4/ the delay in triggering the disease: some treatments delay the appearance of symptoms but to the detriment of the ability to overcome the disease;

5/ the rate of animals becoming sick.

These evaluations are carried out by a duly qualified veterinarian trained in the context of an experimental protocol usually implemented with the aim of evaluating performance levels of vaccines against IB.

Experimental Results

Antibody Titers:

The set of results is presented in table II.

The group of nonvaccinated animals (group 13) does not significantly produce antibodies (approximately 1 with a standard deviation of approximately 0.2), which means that there was no contamination with the virus during the trial, thus validating the other results.

The commercial vaccine (group 12) produces titers greater than 3 after 28 days, with a standard deviation of approximately 0.2 as early as 14 days after vaccination and which is stable for 56 days.

Groups 1/3/5/7/9 produce antibody titers greater than 3 (up to 4) starting from 21 days and throughout the duration of the trial, with standard deviations of approximately 0.2.

These groups show results that are significantly better compared with the commercial vaccine (P noted in the table).

The other groups show response levels similar to or less than the commercial vaccine.

P defines the significance of the results, that is to say the probability of occurrence which makes it possible to establish whether the differences are significant.

P<0.01: significant difference compared with the commercial vaccine.

P<0.001: very significant difference compared with the commercial vaccine.

TABLE II

Results of antibody titers of groups 1 to 13 before virulent challenge, for 56 days

| | Before vaccination | \[Days after vaccination\] 7 | 14 | 21 | 28 | 35 | 42 | 49 | 56 |
|---|---|---|---|---|---|---|---|---|---|
| Group 1 | 2.11 ± 0.13 | 1.40 ± 0.23 | 2.31 ± 0.13 | 2.65 ± 0.07 | 2.89 ± 0.13 | 3.19 ± 0.13 | 3.99 ± 0.04 ($P < 0.001$)** | 4.01 ± 0.04 ($P < 0.001$) | 3.76 ± 0.08 ($P < 0.001$) |
| Group 2 | 1.46 ± 0.27 | 1.18 ± 0.25 | 2.42 ± 0.12 | 2.60 ± 0.14 | 3.22 ± 0.17 | 3.23 ± 0.14 | 3.21 ± 0.15 | 3.24 ± 0.13 | 3.15 ± 0.16 |
| Group 3 | 2.11 ± 0.13 | 1.40 ± 0.23 | 2.31 ± 0.13 | 2.65 ± 0.07 | 2.89 ± 0.13 | 3.19 ± 0.13 | 3.99 ± 0.04 ($P < 0.001$)** | 4.01 ± 0.04 ($P < 0.001$) | 3.76 ± 0.08 ($P < 0.001$) |
| Group 4 | 2.08 ± 0.23 | 1.39 ± 0.29 | 2.48 ± 0.15 | 2.74 ± 0.2 | 2.55 ± 0.44 | 3.03 ± 0.18 | 3.10 ± 0.14 | 3.11 ± 0.19 | 3.68 ± 0.11 ($P < 0.001$) |
| Group 5 | 1.68 ± 0.32 | 1.85 ± 0.22 | 2.61 ± 0.17 | 3.24 ± 0.17 | 3.64 ± 0.10 ($P ≤ 0.01$) | 3.72 ± 0.10 ($P < 0.02$) | 3.70 ± 0.11 ($P < 0.001$) | 3.48 ± 0.14 | 3.22 ± 0.16 |
| Group 6 | 1.40 ± 0.27 | 0.68 ± 0.25 | 2.55 ± 0.18 | 2.97 ± 0.21 | 2.90 ± 0.20 | 3.05 ± 0.12 | 3.01 ± 0.13 | 2.92 ± 0.15 | 2.82 ± 0.17 |
| Group 7 | 1.91 ± 0.29 | 1.44 ± 0.22 | 2.84 ± 0.14 | 2.90 ± 0.17 | 3.24 ± 0.20 | 3.90 ± 0.05 ($P < 0.001$) | 3.90 ± 0.05 ($P < 0.001$) | 3.69 ± 0.08 ($P < 0.01$) | 3.46 ± 0.1 ($P < 0.01$) |
| Group 8 | 1.60 ± 0.25 | 1.91 ± 0.14 | 2.77 ± 0.19 | 3.11 ± 0.22 | 3.28 ± 0.21 | 3.38 ± 0.17 | 3.23 ± 0.19 ($P < 0.01$) | 3.20 ± 0.14 | 3.06 ± 0.17 |
| Group 9 | 1.62 ± 0.22 | 1.75 ± 0.20 | 2.81 ± 0.23 | 3.43 ± 0.16 | 3.74 ± 0.32 ($P ≤ 0.01$) | 3.82 ± 0.15 ($P < 0.02$) | 3.75 ± 0.19 ($P < 0.001$) | 3.48 ± 0.14 | 3.22 ± 0.16 |
| Group 10 | 1.97 ± 0.10 | 1.33 ± 0.18 | 2.62 ± 0.12 | 2.91 ± 0.12 | 3.14 ± 0.11 | 3.09 ± 0.15 | 3.08 ± 0.14 | 2.85 ± 0.13 | 2.63 ± 0.14 |
| Group 11 | 1.11 ± 0.13 | 1.54 ± 0.08 | 2.32 ± 0.23 | 3.01 ± 0.11 | 3.04 ± 0.21 | 3.11 ± 0.12 | 3.12 ± 0.19 | 2.52 ± 0.23 | 2.53 ± 0.54 |
| Group 12 commercial vaccine | 1.72 ± 0.21 | 1.42 ± 0.29 | 2.58 ± 0.18 | 2.81 ± 0.17 | 3.15 ± 0.14 | 3.27 ± 0.13 | 3.09 ± 0.10 | 3.11 ± 0.15 | 3.07 ± 0.04 |
| Group 13 Untreated animals | 1.65 ± 0.26 | 0.50 ± 0.21 | 1.00 ± 0.22 | 0.44 ± 0.23 | 0.79 ± 0.20 | 0.80 ± 0.21 | 0.76 ± 0.18 | 0.58 ± 0.24 | 0.38 ± 0.21 |

Virulence Challenge:

TABLE III

Results of behavior in response to the virulent challenge of groups 1 to 13 for the virus-resistance scores

| Group | Number of chickens | Cumulative points | Cumulative days of clinical symptoms | Mean of points/chicken ± standard deviation | Mean delay in start of symptoms ± standard deviation | Proportion triggering the disease |
|---|---|---|---|---|---|---|
| 1 | 10 | 2 | 2 | 0.20 ± 0.38 | 0.20 ± 0.42 | 0.40 |
| 2 | 10 | 32 | 11 | 3.2 ± 0.71 | 3.39 ± 2.84 | 0.80 |
| 3 | 10 | 2 | 3 | 0.20 ± 0.11 | 0.20 ± 0.32 | 0.10 |
| 4 | 10 | 34 | 33 | 3.40 ± 2.80 | 3.30 ± 2.75 | 0.90 |
| 5 | 10 | 5 | 5 | 0.50 ± 0.70 | 1.00 ± 0.71 | 0.30 |
| 6 | 10 | 13 | 12 | 1.30 ± 0.28 | 1.90 ± 0.88 | 0.60 |
| 7 | 10 | 3 | 3 | 0.30 ± 0.48 | 0.30 ± 0.48 | 0.30 |
| 8 | 10 | 12 | 11 | 1.20 ± 0.88 | 1.10 ± 0.88 | 0.70 |
| 9 | 10 | 2 | 2 | 0.20 ± 0.42 | 0.20 ± 0.42 | 0.30 |
| 10 | 10 | 12 | 11 | 1.20 ± 1.23 | 1.10 ± 1.29 | 0.70 |
| 11 | 10 | 8 | 8 | 0.80 ± 1.03 | 0.80 ± 1.03 | 0.50 |
| 12 commercial vaccine | 9 | 22 | 21 | 2.44 ± 1.94 | 2.33 ± 1.73 | 0.50 |
| 13 Negative control | 12 | 109 | 83 | 9.08 ± 1.83 | 6.92 ± 1.44 | 1.00 |

The untreated control group (group 13) produces very high symptom strength scores (approximately 9 per chicken, for 100% of the animals, with many days of disease, and a delay in the triggering of the symptoms of the disease of approximately 7 days). These results validate the virulent challenge.

The use of the commercial vaccine (group 12) significantly reduces all these parameters, with, however, 50% of the chickens still developing the disease, after only two days of delay, but with moderate symptoms (22 cumulative points) for a relatively short period of time (only 21 cumulative days).

Groups 1/3/5/7/9 show very low cumulative point scores (0.2 to 0.5) for short periods of time (2 to 5 cumulative days) without significantly delaying the symptoms of the disease and while protecting at least 60% of the population in each group.

The other groups give intermediate scores between the commercial vaccine and groups 1/3/5/7/9, but without inducing protection greater than 50% of the population.

The invention claimed is:

1. A method for preparing a vaccine composition for an avian viral disease, the method comprising extemporaneously mixing a vaccine comprising at least one live virus belonging to one or more strains of IBV (infectious bronchitis virus), with an adjuvant diluent,
wherein said adjuvant diluent is an oil-in-water emulsion comprising, for 100% of its weight:
from 50% to 97% of water,
from 1% to 45% of oily adjuvant,
from 0.1% to 10% of at least one divalent inorganic salt, and
from 0.1% to 10% of at least one complexing agent.

2. The method according to claim 1, wherein the virus is freeze-dried before said extemporaneously mixing the vaccine.

3. The method according to claim 1, wherein said oily adjuvant comprises, for 100% of its weight:
from 40% to 95% of at least one mineral oil, and
from 5% to 60% of at least one surfactant.

4. The method according to claim 1, wherein said at least one divalent inorganic salt is selected from the group consisting of manganese gluconate, calcium gluconate, calcium aspartate, zinc gluconate, iron gluconate, and calcium chloride.

5. The method according to claim 1, wherein said at least one complexing agent is selected from the group consisting of ethylenediaminetetraacetic acid (EDTA), sodium gluconate, potassium gluconate, and sodium polyacrylate.

6. The method according to claim 1, wherein said adjuvant diluent is an oil-in-water emulsion comprising, for 100% of its weight:
from 80% to 97% of water,
from 2% to 10% of oily adjuvant,
from 0.2% to 3% of at least one divalent inorganic salt, and
from 0.2% to 3% of at least one complexing agent.

7. The method according to claim 1, wherein said oily adjuvant comprises, for 100% of its weight:
from 50% to 90% of at least one mineral oil, and
from 10% to 50% of at least one surfactant.

8. The method according to claim 6, wherein said oily adjuvant comprises, for 100% of its weight:
from 50% to 90% of at least one mineral oil, and
from 10% to 50% of at least one surfactant.

* * * * *